(12) United States Patent
Singer et al.

(10) Patent No.: US 7,128,746 B2
(45) Date of Patent: Oct. 31, 2006

(54) DEVICE FOR TREATING INTERVERTEBRAL DISC HERNIATIONS

(75) Inventors: Deron J. Singer, Burnsville, MN (US); Eric F. Caillé, Minnetonka, MN (US); Merrill W. Reuter, Boca Raton, FL (US)

(73) Assignee: PMT Corporation, Chanhassen, MN (US)

( * ) Notice: Subject to any disclaimer, the term of this patent is extended or adjusted under 35 U.S.C. 154(b) by 0 days.

(21) Appl. No.: 10/965,988

(22) Filed: Oct. 15, 2004

(65) Prior Publication Data

US 2005/0049604 A1 Mar. 3, 2005

Related U.S. Application Data

(63) Continuation-in-part of application No. 10/147,580, filed on May 16, 2002, now Pat. No. 6,805,715.

(51) Int. Cl.
*A61B 17/58* (2006.01)

(52) U.S. Cl. ...................................... 606/90

(58) Field of Classification Search ............... 606/61, 606/90, 92–94, 105; 604/30, 33, 34, 99.03, 604/99.04, 67.03
See application file for complete search history.

(56) References Cited

U.S. PATENT DOCUMENTS

| | | | | |
|---|---|---|---|---|
| 3,503,400 | A | * | 3/1970 | Osthagen et al. ............ 604/249 |
| 4,685,447 | A | | 8/1987 | Iversen et al. |
| 4,946,449 | A | * | 8/1990 | Davis, Jr. .................... 604/256 |
| 5,707,357 | A | * | 1/1998 | Mikhail et al. ......... 604/167.03 |
| 5,972,015 | A | | 10/1999 | Scribner et al. |
| 6,056,721 | A | * | 5/2000 | Shulze ................... 604/101.05 |
| 6,066,154 | A | | 5/2000 | Reiley et al. |
| 6,224,630 | B1 | | 5/2001 | Bao et al. |
| 6,235,043 | B1 | | 5/2001 | Reiley et al. |
| 6,248,110 | B1 | | 6/2001 | Reiley et al. |
| 6,280,456 | B1 | | 8/2001 | Scribner et al. |
| 6,616,673 | B1 | * | 9/2003 | Stone et al. ................. 606/105 |
| 6,749,614 | B1 | * | 6/2004 | Teitelbaum et al. ........... 606/61 |
| 6,852,095 | B1 | * | 2/2005 | Ray ........................ 604/93.01 |

(Continued)

*Primary Examiner*—Eduardo C. Robert
*Assistant Examiner*—Michael J. Araj
(74) *Attorney, Agent, or Firm*—Anthony G. Eggink; Katrina M. Eggink

(57) ABSTRACT

A method and device for treating human intervertebral disc herniations using an endoscopic procedure. An access port is opened into and through the annulus of a disc to remove nucleus pulposus. Subsequent treatment, a balloon device having a valve structure is positioned via an endoscopic procedure into the disc space. The balloon device is filled with a physiological fluid to occupy the disc interspace or to maintain some degree of distraction of the created disc space. Post surgery, after fibrocollagenous tissue has grown into the disc space, a second endoscopic procedure is performed to remove the balloon device. Fluid is removed to collapse the balloon structure and then removed via the guide tube. The ingrowth of fibrocollagenous tissue will continue to fill the void formerly occupied by the balloon device. The balloon device has a rigid valve body and a flexible balloon member. The valve body has an end plug, a valve chamber holding a valve member and a cooperating biasing structure. The balloon member of the device is inserted into a vacated nucleus space of a herniated disc and then inflated with a physiological fluid using a fill tube. The balloon member, valve body, and fill tube or portions thereof may be constructed of a radiolucent material to provide visibility during implantation, surveillance and removal. The balloon device may be used in the cervical, lumbar or thoracic region of the spine.

19 Claims, 3 Drawing Sheets

U.S. PATENT DOCUMENTS 6,926,729 B1 * 8/2005 Sell et al. .................. 606/192

2003/0033017 A1 2/2003 Lotz et al.

* cited by examiner

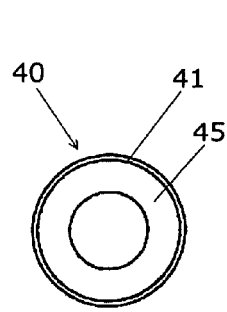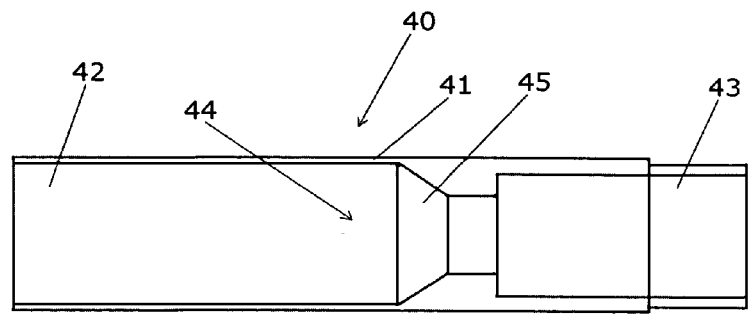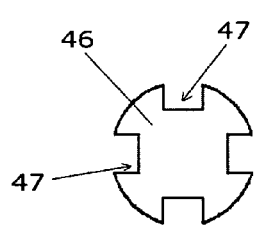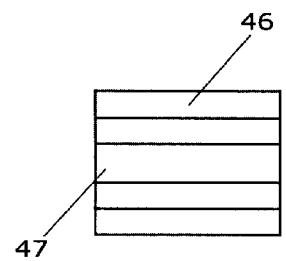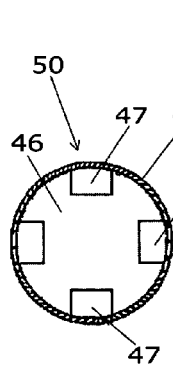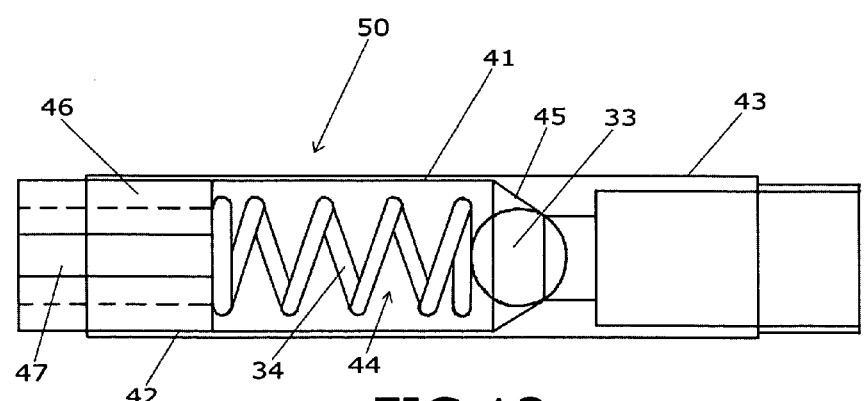

DEVICE FOR TREATING INTERVERTEBRAL DISC HERNIATIONS

This application is a continuation-in-part of U.S. patent application entitled "Method and Device for Treating Intervertebral Disc Herniations", having Ser. No. 10/147,580 and filed on May 16, 2002 U.S. Pat. No. 6,805,715. The '580 Patent application is fully incorporated by reference herein.

BACKGROUND OF THE INVENTION

The present invention relates generally to a method and device for treating intervertebral disc herniations using an endoscopic procedure. Particularly, this invention relates to a distraction disc anthroplasty device and method for treating intervertebral disc herniations. More particularly, the present invention relates to treating intervertebral disc herniations using a temporary flexible balloon device in the treated disc to alleviate pressure between adjacent vertebrae located in the cervical, thoracic, or lumber areas of the spine.

Intervertebral disc herniations are a major source of back pain. Herniations and ruptures of intervertebral discs may also cause pain and numbness in the leg, feet and arms of affected patients. Herniated, or ruptured, discs may be caused by traumatic injury due to accident, illness, the aging process as well as a multiplicity of undefined causes.

Intervertebral discs are located between adjacent vertebrae of the spine and are comprised of an annulus portion surrounding the nucleus pulposus or pulp. A herniation of an intervertebral disc results from a weakened, torn or stretched area of the annulus. Pulp from the nucleus extrudes through the herniated area in the annulus producing pressure on the spinal column and/or adjacent nerves and thereby causing pain. Removing the pulp reduces pressure on the spinal column or adjacent nerves caused by the herniation.

In the past, intervertebral disc injuries have been treated with implantable disc spacers, for example. The use of these prior art devices do not account for several procedural variables, for example, a patient's intervertebral spacing, vacated nucleus volume, variability in spacer volume, or mismatch of spacer size to the patient. The prior art methods also typically involve invasive surgery which require relatively long recovery times for the patient.

It is an object of this invention to provide a minimally invasive interposition arthoplasty procedure utilizing an inflatable distraction device which allows for short-term recovery from surgery and the patient's early return to normal activity.

SUMMARY OF THE INVENTION

The present invention relates to method and device for treating a herniated intervertebral disc. The intervertebral disc may be located in the cervical, thoracic or lumbar area of the spine.

The inflatable distraction device of the present invention comprises a valve body having an inflatable balloon member. The rigid valve body has a valve chamber having a valve means comprising a ball valve member and cooperating biasing member. The valve body is in communication with a fill tube connected to the valve body which provides the ingress and egress of a physiological fluid to inflate and deflate the inflatable balloon member. The valve body may have a valve plug portion which is slotted to allow the passage of fluid. The ball valve member is constructed and arranged to seal the fill tube connected to the valve body due to the pressure created from the biasing spring and internal fluid pressure of the balloon member.

The balloon member is preferably constructed of silicone or the like. The valve body portion is preferably constructed of a rigid material, for example titanium, a polymeric material or a like material. In the assembly of the inflatable distraction device, the fill tubing may be inserted into and secured, for example using an adhesive, to the inside of one end of the valve body. The valve plug portion may be inserted, i.e., threaded, into the opposite end of the valve body and the entire structure is then inserted into the open end of the flexible balloon member and adhered in place.

It is an object of the present invention to provide an inflatable balloon device which is temporarily positioned into the treated cavity of an interveterbral disc. The balloon member may be inflated and expanded by injecting a fluid into the balloon, for example, a normal saline solution. A fill tube, connected to the valve body, is provided to permit the balloon to be filled with the fluid. When the balloon member is inflated, it occupies and distracts the cavity volume of the disc which allows the expanded balloon member to carry the loads of the vertebra and minimizes the compression on the healing annulus and nucleus due to vertebral motion or compressive bulging of the inflated balloon. By not disturbing the healing tissue, the healing process may proceed more swiftly.

The balloon device includes a fill tube for fluid transport to inflate the balloon member. The fill tube preferably remains limp and is easily deformed such that it may be easily implanted. The fill tube may be removable from the body portion of the balloon assembly or it may remain connected to the balloon member or may be cut to a desired length subsequent the placement of the balloon member into the disc cavity.

The method of the invention includes an endoscopic procedure to create an access port in the annulus portion of the herniated or ruptured intervertebral disc. Using a guide tube through the access port, pulp is removed from the nucleus area of the disc. Next, the tissues of the inner surface of the annulus may be annealed to shrink and tighten the annulus so that any ruptured or injured areas can continue the ingrowth process of fibrocartiligenous tissue deposition. A natural or synthetic material may be placed into the disc space in order to promote tissue growth. A balloon device having a valve is inserted into the disc space via the endoscopic guide tube. The balloon portion is then filled with fluid to distract the adjacent vertebrae or to occupy a portion of the intervertebral disc space. The guide tube is then removed from the access port. When fibrocollagenous tissue has grown into the distracted space, usually a few months to a few years, another endoscopic procedure is performed to remove the balloon device.

The balloon device may include a nubbin or end portion which may be incorporated into the balloon device structure to engage and maintain the access port in the disc annulus. The nubbin and/or other portions of the balloon device structure may be radiolucent to improve visualization of the balloon assembly during insertion, expansion and removal. Alternatively, the balloon device may be constructed of a dissolvable material.

The balloon member of the device, the end portion and the fill tubing may be constructed of a MRI and CT compatible material and which is radiolucent or may have radiolucent markings to permit increased visualization of the assembly during implant or removal surgery or observation during the healing process.

An object of the present invention is to provide a balloon device for treating intervertebral disc herniations, known as a major source of back pain. It is an object of the invention to provide a balloon device which can be inserted using a minimally invasive procedure and which allows for short-term recovery from surgery and the patient's early return to normal activity. It is a further object of this invention to provide a balloon device which distracts the cavity space by providing a constant pressure and thus minimizing the compression of the healing annulus and nucleus. It is a further object of this invention to provide a balloon device which can be easily located during surgery for either insertion, expansion or removal the device.

Another object of the invention is to improve visualization of the balloon assembly during insertion, expansion and removal from the intervertebral disc space. A further object of the invention is to promote tissue ingrowth in the intervertebral disc space.

These and other benefits of this invention will become clear from the following description by reference to the drawings.

BRIEF DESCRIPTION OF THE DRAWINGS

FIG. 9 is a lateral sectional view of an alternative valve body structure;

FIG. 10 is an end view of the valve body structure of FIG. 9;

FIG. 11 is a lateral view of the valve end plug used with the valve body structure;

FIG. 12 is an end view of the valve end plug of FIG. 11;

FIG. 13 is a lateral sectional view of an alternate assembled valve body; and

FIG. 14 is an end view of the valve body of FIG. 13.

DESCRIPTION OF THE PREFERRED EMBODIMENTS

The present invention relates to a method and device for treating intervertebral disc herniations using endoscopic procedure. The method provides a minimally invasive procedure which allows for short-term recovery from surgery and a patient's early return to normal activity.

Figure 1:
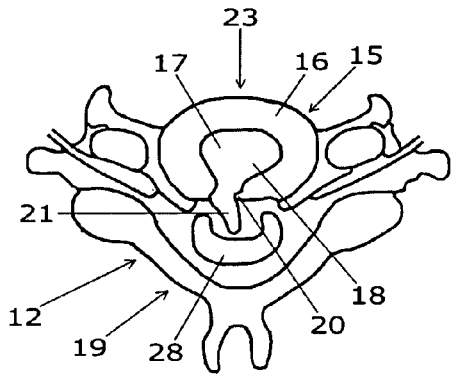
FIG. 1 is a top sectional view showing a ruptured intervertebral disc.

FIG. 1 shows a top sectional view of a herniated disc 15 of a spine 12. Spine 12 is shown to have a vertebral canal 28 and having posterior region 19 and anterior area 23. Disc 15 is shown having annulus portion 16 surrounding nucleus portion 17. Nucleus portion 17 is made up of pulp 18. The disc 15 is shown to be herniated or ruptured at herniation 20, whereby pulp 21 is shown extruding from nucleus 17 and through annulus 16 into the posterior region 19 of the spine thereby causing pain to the patient. The expressed or extruded pulp 21 from the disc space may be an irritant to nerve tissue that lie posterior to the vertebral column and may be a cause of back pain. It may also be the cause of referred pain and numbness to affected arm, hand, leg or foot areas.

Figure 2:
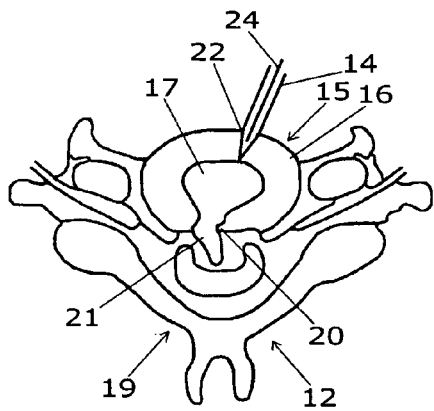
FIG. 2 is a top sectional view showing a guide tube advanced through the access port in the anterior of the disc annulus.
Figure 3:
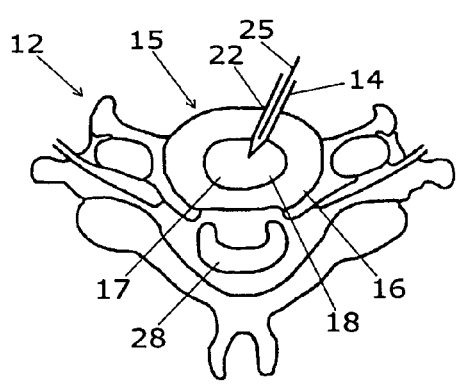
FIG. 3 is a top sectional view showing the pulp removed from the disc.

The endoscopic procedure initially involves a surgical skin incision of approximately 3 mm in the skin and through which an endoscopic guide tube 14 is passed. FIG. 2 shows guide tube 14 inserted into disc 15 through annulus 16 and into nucleus 17. Trocar 24 is inserted within the guide tube 14 and is used to aide in forming access port 22 so that extruded pulp 21 may be removed. FIG. 3 shows pulp 18 being removed from the disc interspace through guide tube 14. The guide tube 14 is preferably a long radiolucent needle-like probe having an internal diameter of about 2.5 millimeters. The guide tube 14 is manually guided by imaging technique to the proposed entry or access port 22 to be created in the targeted annulus. The access port 22 then allows for removal of the nucleus pulposus. Disc removal instrument or grasper 25 is shown within the guide tube 14 to remove the pulp 18.

The annulus 16 may next be laser annealed to cause shrinking and tightening of the tissues of the annulus 16 to reduce the size of any lateral or posterior tears in the annulus from which nucleus pulposus 18 may have expressed out from the intervertebral disc space.

Figure 4:
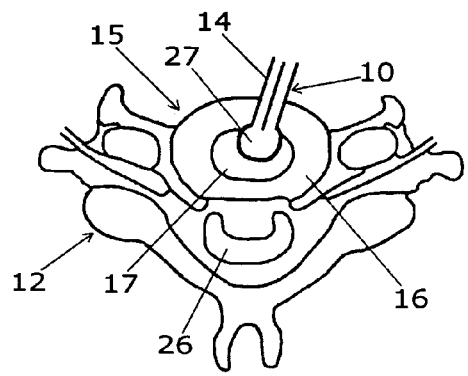
FIG. 4 is a top sectional view showing the balloon assembly expanded by a fluid.
Figure 5:
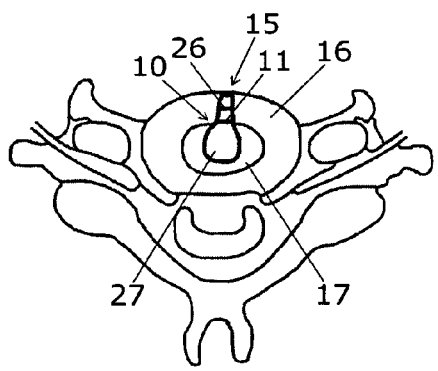
FIG. 5 is a top sectional view showing the filled balloon structure and the instrumentation removed.
Figure 6:
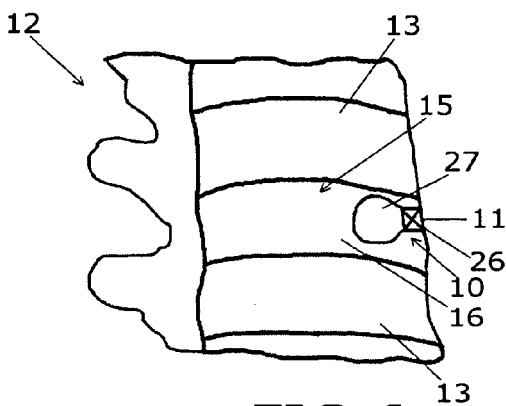
FIG. 6 is a lateral sectional side view showing the filled balloon maintaining distraction of the adjacent vertebrae.

FIG. 4 shows balloon device or assembly 10 being inserted through guide tube 14 and into nucleus 17. Expandable balloon structure 27 is shown within the disc 15 of spine 12. FIGS. 7–13 show another valve device embodiment and components thereof and which is further described below. FIGS. 5 and 6 show balloon assembly 10 secured in disc 15 with the guide tube and instrumentation removed through the incision. Disc 15 is shown positioned between vertebrae 13 of spine 12. The nubbin or end portion 11 of balloon assembly 10 is shown secured in the annulus 16. Balloon assembly 10 is shown having valve 26 in nubbin 11 and an expandable balloon structure 27.

The nubbin 11 (uninflatable portion of the balloon assembly) or other portions of the entire balloon assembly 10 may be radiolucent in order to make it easier to locate during the endoscopic procedures. Alternatively, the balloon assembly 10 may have radiolucent markers added thereto for purposes of locating and maneuvering the assembly 10 during the process steps of the invention. Further, the balloon structure may utilize silicone pigments or expansion fluid which is radiolucent. The balloon assembly 10 is also preferably constructed of MRI and CT compatible materials. A physiologically compatible fluid such as physiological normal saline or the like is preferably used to fill the balloon via the valve. The filled balloon distracts the adjacent vertebrae 13 thereby providing structure in the void or space formerly filled with the removed pulp. The filled balloon may also occupy the intervertebral disc space after the pulp has been removed, whereby the space is substantially occupied.

Figure 7:
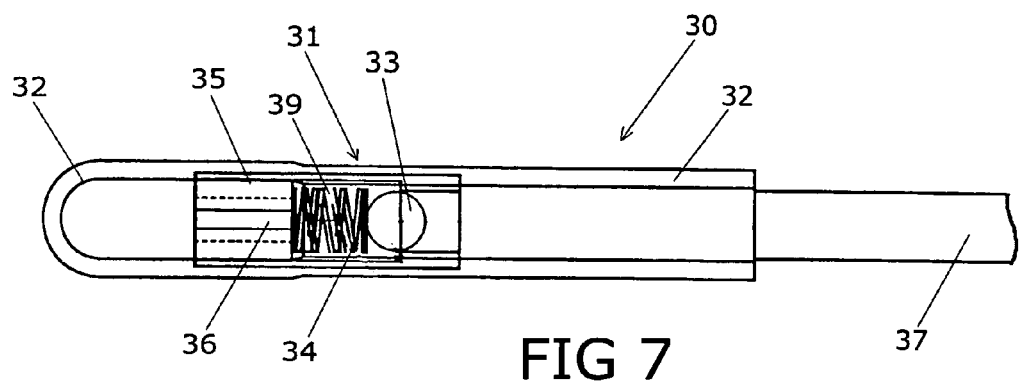
FIG. 7 is an enlarged lateral view showing an embodiment of the balloon device of the present invention.
Figure 8:
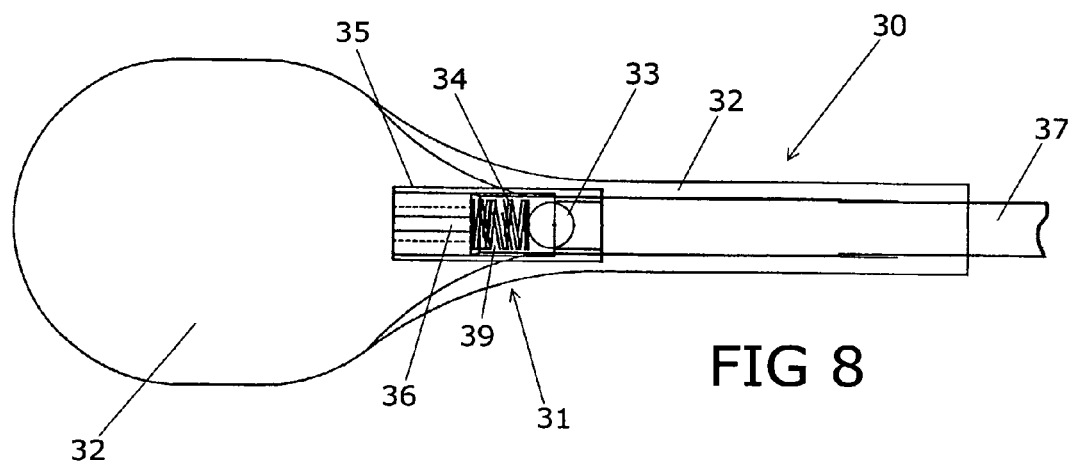
FIG. 8 is an enlarged lateral view showing the embodiment of the balloon device of FIG. 7 and showing the balloon member in an inflated state.

As shown in FIG. 7, the inflatable balloon device embodiment 30 of the invention comprises a rigid body portion 31 and a flexible balloon member 32. The rigid body portion 31 is shown having a valve chamber 39 containing a ball valve member 33, a biasing spring member 34, and a valve plug portion 35 positioned at one end. The valve plug portion 35 is shown having slots 36, which are constructed and arranged to allow the passage of fluid. A fill tube 37 is shown extending from the opposite end of rigid body portion 31 and is constructed and arranged to provide fluid flow through the valve plug 35 in order to inflate and deflate the balloon member 32. The ball valve member 33 is constructed and arranged to seal the fill tube 37 due to the pressure created from the spring 34 and internal pressure of the balloon member 32. FIG. 8 shows the balloon member 32 in an inflated state. In the inflated or expanded state, the balloon member 32 is shown separated from a portion of the valve body structure 31. The balloon member 32 is further shown being connected or adhered to the remainder of the valve body 32 exterior and to the exterior of the fill tube 37.

As shown in FIGS. 9 and 10, an alternate valve body embodiment 40 is shown having a valve body structure 41 having opposing ends 42 and 43. The valve body 41 has a valve chamber 44, which begins at the internally sloped valve seat 45. FIGS. 11 and 12 show valve end plug 46 which is shown inserted in end 42 of the valve body 41. The end plug 46 has a plurality of slots or channels 47 which permits the passage of fluid as described above. The end plug may be threaded into or otherwise secured in the end of the valve body 41. Although the slots or channels 47 are shown peripherally located on the end plug 46, the channels may extend through the end plug body.

FIGS. 13 and 14 show the assembled valve body 50 having ball valve 33 located in the sloped valve seat 45 and the biasing spring member 34 positioned between the end plug 46 and the ball valve 33. In a similar manner, as described above, the fill tube 37 is inserted and secured in the end portion 43 of the valve body 41 and subsequently the balloon member 32 is positioned over the assembled valve body 50 and secured, i.e., via an adhesive to the valve body end 43 and to the exterior of the fill tube 37 (not shown). Although a ball valve/biasing spring arrangement is shown and discussed herein, other valve means may be used in the balloon assembly and are within the purview of the invention.

In assembling the balloon device 30, the fill tubing 37 may be inserted into and glued within the end of the valve body 31. The valve body 31 is then assembled and is inserted up into the DDA (distraction device arthoplasty) Balloon and adhered in place via an adhesive, for example.

The balloon member 32 is preferably constructed of silicone or the like. The valve body portions 31 and 41 and the valve plug portions 35 and 46 are preferably constructed of a rigid material, for example titanium, a polymeric material or like material. The ball valve member 33 is preferably made of Teflon (polytetraflouro-ethylene) or a like material. The biasing spring member 34 may be constructed of nickel, for example.

It is within the purview of this invention to utilize a balloon device constructed of a dissolvable material composition. The utilization of a dissolvable balloon structure, which preferably would dissolve in a specified time period, would alleviate the need of the subsequent removal of the balloon assembly from the patient.

Prior to the placement of the balloon device, a medically suitable option such as powdered hydroxyapatite or cell culture material or the like to facilitate the ingrowth of structured tissue in the intervertebral space formerly occupied by the removed pulp may be used. Homologous tissue cell culture seeding may also be used to facilitate the ingrowth of structured tissue in the distracted space.

After removing the endoscopic instruments the approximately 3 millimeter skin incision is closed by suture, staple, bonding agent, adhesive bandage, or like procedure. After about 1 month to about 3 years, when fibrocollagenous tissue has grown into the intervertebral disc space, a second endoscopic procedure is performed to remove the balloon assembly 10. In this endoscopic procedure the fluid is removed from the balloon structure, i.e., by opening the ball valve by pushing the valve from the valve seat with an instrument, and the balloon is then removed via the guide tube 14 and through the port in the annulus that the nubbin (uninflated portion of balloon device) or valve body has kept patent or open. An imaging technique facilitates guiding the endoscopic guide tube to the radiolucent nubbin.

Finally, after all endoscopic instruments are removed, suture, bonding agent, adhesive bandage or like procedure is used to close the skin incision.

The procedure of the invention employs a minimally invasive endoscopic procedure which provides for a reduced cost, less time involved surgical procedure, and a patient's short term surgical recovery and early return to normal activity. The procedure can be performed at all areas of the spine, including cervical, thoracic and lumbar areas.

A more detailed description of the procedure as applied to an anterior cervical discectomy is set forth in the '580 Patent Application which is incorporated by reference herein.

The process steps of the procedure may be monitored under fluoroscopic guidance down to the anterolateral aspect of the annulus. The cannula, (i.e., 3 mm diameter) and the dilator are both replaced seating the cannula on the anterior annulus. The 2.5 millimeter trephine is then inserted into the interspace under fluoroscopic guidance providing an anterior anulotomy. The trephine and trochar are then removed. The 2.5 millimeter disc removal instrument is placed into the central region of the disc and the position confirmed with fluoroscopy. The 2.5 millimeter grasper is then employed to remove the trephine annular core if the disc removal instrument did not evacuate it. Irrigation and aspiration of the disc with resection is then commenced with approximately 1 to 3 cubic centimeters of disc material collected in about 20 to 30 minutes of combined aspiration and cutting. The discectomy is focused in the posterior region of the interspace in the area of the predominant disc herniation. Once a quantitative amount of contrast agent and disc material is removed the graspers are used to remove any free fragments.

Following the latter step the flexible LASE endoscope by Claris Medical Systems, Inc., Minneapolis, Minn., U.S.A., or the like is then placed into the interspace with the position confirmed by fluoroscopy and direct vision. Using direct vision, laser discoplasty is accomplished with 800 to 1500 kilojoules using holmium laser by New Star Lasers, Roseville, Calif., U.S.A. or the like. Under endoscopic visualization the posterior annulus fibers are identified and treated. Additional laser modulation in the uncinate regions further stabilizes the segment and decreases discogenic neuroforaminal encroachment.

Under fluoroscopic guidance, the balloon assembly is then inserted into the anterior aspect of the interspace and then inflated. Spinal monitoring is utilized continuously introperatively to confirm satisfactory response and no neurologic changes. The balloon device position is then confirmed by direct endoscopic and fluoroscopic evaluation. The interspace is irrigated and the instruments are removed. A Philadelphia firm collar or like cervical collar may then be placed onto the patient.

While the above described procedure offers patients an additional 5 or 10 years or more without spinal fusion, this procedure, employing the distracted disc arthroplasty device, not only lessens the stresses on adjacent vertebral disc segments but leaves open the possibility of procedure to place a functional prosthetic device that may very likely appear in the near future.

After about a few weeks to about a few years post surgery when fibrocollagenous tissue has grown into the distracted space another endoscopic procedure is performed to remove the balloon device, i.e., deflating the balloon member using a stylette on the ball valve to open the valve structure. This second procedure removes fluid from the balloon device to deflate the device for removal via the access port in the annulus. The ingrowth of fibrocollagenous tissue continues to fill the intervertebral disc space that has been vacated by the removal of the balloon device.

In summary, the present invention is a method and assembly which permits surgery for a disc herniation which is relatively non-invasive and which permits the patient a relatively short recovery time. An access port is created in the annulus portion of a herniated intervertebral disc. Using a guide tube through the access port, extruded pulp is removed from the herniated disc and the annulus may be annealed to aide healing. A balloon assembly is inserted through the guide tube into the nucleus portion of the disc for distraction or occupation of the intervertebral disc space. The balloon assembly may be utilized with a material which acts as a fibrocartiligenous seeding material to enhance the surgical outcome. The balloon assembly is filled with a physiologically compatible fluid to expand it for occupation and distraction purposes. The balloon assembly may have a nubbin, which is secured in the annulus of the disc to ensure that the balloon assembly stays in place and permit easy access to the balloon assembly for removal. The balloon assembly elements, such as the nubbin may be radiolucent to improve visualization of the assembly during insertion, expansion and removal processes. Further, the balloon assembly may be constructed of a dissolvable physiologically compatible composition which would dissolve over a specified period of time to provide support in the disc space at the time of insertion and to dissolve during and after the ingrowth of tissue. This latter structure would alleviate the need for the subsequent balloon assembly removal procedure.

The inflatable distraction device of the invention may have a diameter ranging between 1 mm to 6 mm in its uninflated state, i.e., 1.5–2.5 mm. When inflated, the balloon member of the distraction device accommodates the disc space and which may require 2 cc of fluid, for example, to expand and inflate to a diameter of 1 cm or larger to thereby distract the disc cavity. Although the valve body of the device may be rigid, alternatively, the valve body member may be constructed of a semi rigid polymeric material or the like. The required rigidity of the valve body structure depends upon the proper function and operability of the valve means, which, as discussed above, may be a biased ball valve or any other valve structure capable of one-way valve operation and having means to permit egress of fluid for collapsing the balloon member.

As many changes are possible to the method and embodiments of the assemblies of this invention utilizing the teachings thereof, the descriptions above, and the accompanying drawing should be interpreted in the illustrative and not in the limited sense.

That which is claimed is:

1. An inflatable distraction device for insertion into the cavity of an intervertebral disc of the spine of a patient, said inflatable distraction device comprising:
    a) an elongated, valve body structure having a first end, a second end, said valve body having a valve chamber with a valve member mounted therein and further having an end plug in said first end of said valve body, said end plug having at least one channel member, said valve member comprising a ball valve and biasing means positioned in said valve chamber of said valve body;
    b) a flexible, expandable balloon member extending from said first end of said valve body structure, said balloon member being constructed and arranged to receive a fluid through said valve body and to occupy the cavity in the intervertebral disc;
    c) a flexible fill tube connected to said second end of said valve body structure; and
    d) said end plug being peripherally slotted and threadingly positioned in said first end of said valve body structure, said valve body structure further having a truncated, sloped portion forming a valve seat in said valve chamber of said valve member.

2. The inflatable distraction device of claim 1, wherein said device has a diameter between approximately 1 mm and 6 mm in its uninflated state, wherein said flexible fill tube has an end which is fastened within said second end of said valve body structure, wherein said end plug is positioned in communication with said biasing means.

3. The inflatable distraction device of claim 1, wherein a physiological fluid is inserted through said fill tube and valve body and into said expandable balloon member.

4. The inflatable distraction device of claim 3, wherein said valve body structure is constructed of titanium or a rigid polymeric material, wherein said balloon member is constructed of silicone and wherein said valve member is constructed of a polymeric material.

5. The inflatable distraction device of claim 1, wherein said inflatable distraction device is constructed of a MRI and CT compatible material, and wherein at least a portion of said expandable balloon assembly is marked with or constructed of a radiolucent material.

6. The inflatable distraction device of claim 1, wherein said device is constructed and arranged to be inserted into and removed from the cavity of an intervertebral disc via an endoscopic procedure.

7. The inflatable distraction device of claim 1, wherein said fill tube is mounted within said second end of said valve body and wherein said balloon member is secured over and to a portion of said valve body and a portion of said fill tube.

8. The inflatable distraction device of claim 1, wherein said balloon member is expanded to occupy and distract the disc space by providing an outward force within the disc cavity, wherein said balloon member is positioned in the disc cavity for a period of time and removed subsequent the ingrowth of fibrocartiligenous tissue and wherein a brace device is provided to the patient for use in combination with said balloon assembly.

9. The inflatable distraction device of claim 1, wherein said device is constructed of dissolvable material.

10. An expandable balloon device for insertion into the cavity created in an intervertebral disc of the spine of a patient, said balloon device comprising:
    a) a valve body structure having a cylindrical configuration, a first end, a second end, a valve chamber, said valve body structure being constructed and arranged for positioning in the entry of the cavity of the intervertebral disc;
    b) a flexible balloon member attached to said body structure, said balloon member having a finite and fixed volume when expanded with a fluid;
    c) a valve member positioned in said valve chamber of said body structure, said valve member comprising a ball valve and a valve biasing means; and d) a fill tube attached to said second end of said valve body structure, said fill tube remaining implanted in a patient during the healing process.

11. The expandable balloon assembly of claim 10, wherein said valve body structure has a valve seat for said valve member and a biasing spring in said valve chamber adjacent said valve member.

12. The expandable balloon device of claim 10, wherein said fill tube is attached to said body structure and is mounted for removal therefrom.

13. The expandable balloon device of claim 10, wherein said expandable balloon device is constructed of a MRI and CT compatible material, and wherein at least a portion of said expandable balloon assembly is marked with or constructed of a radiolucent material.

14. An expandable balloon assembly for insertion into a treated herniated intervertebral disc cavity, said assembly comprising:
   a) a generally cylindrical valve body structure having a valve chamber, a first end, a second end and being constructed and arranged to be positioned within the intervertebral disc cavity, said valve body further having an end plug positioned in said first end of said valve body structure;
   b) a valve member and biasing means positioned in said valve chamber said biasing means further being in communication with said end plug;
   c) a flexible balloon member connected to one end of said body structure constructed and arranged to expand by receiving a fluid; and
   d) a flexible fill tube connected to said second end of said valve body structure for inserting fluid into said balloon member; wherein said flexible fill tube has an end which is fastened within said second end of said valve body structure.

15. The balloon assembly of claim 14, wherein said assembly is constructed of an MRI and CT compatible material and whereby at least a portion of said balloon assembly is radiolucent.

16. The balloon assembly of claim 14, wherein said valve body and valve member are constructed of titanium or polymeric material and wherein said fill tube and balloon member are constructed of a flexible polymeric material.

17. The balloon assembly of claim 14, wherein said assembly has a diameter between approximately 1 mm and 6 mm.

18. The balloon assembly of claim 14, wherein said fill tube remains implanted in a patient during the healing process.

19. The balloon assembly of claim 14, wherein the fluid is physiological fluid.

* * * * *